United States Patent [19]

Niwa et al.

[11] Patent Number: 4,497,075
[45] Date of Patent: Feb. 5, 1985

[54] FILLER FOR FILLING IN DEFECTS OR HOLLOW PORTIONS OF BONES

[75] Inventors: Shigeo Niwa; Kazuhiko Sawai; Shinobu Takahashi, all of Aichi; Mikiya Ono, Saitama; Yoshiaki Fukuda, Saitama; Hiroyasu Takeuchi, Saitama; Hideo Tagai, Tokyo, all of Japan

[73] Assignee: Mitsubishi Mining & Cement Co., Ltd., Tokyo, Japan

[21] Appl. No.: 353,765

[22] Filed: Mar. 1, 1982

Related U.S. Application Data

[63] Continuation-in-part of Ser. No. 191,894, Sep. 29, 1980, abandoned.

[30] Foreign Application Priority Data

Oct. 8, 1979 [JP] Japan .................. 54-128821

[51] Int. Cl.$^3$ .................. A61F 1/24; C01B 25/32
[52] U.S. Cl. .................. 3/1.9; 106/306; 128/92 R; 128/92 C; 128/92 G; 423/308; 423/309; 423/311; 501/1

[58] Field of Search .................. 423/308, 309, 311; 3/1.9; 106/306; 501/1

[56] References Cited

U.S. PATENT DOCUMENTS

| | | | |
|---|---|---|---|
| 3,737,516 | 6/1973 | Jenner | 423/308 |
| 4,046,858 | 9/1977 | Barsa et al. | 423/311 |
| 4,097,935 | 7/1978 | Jarcho | 501/151 |
| 4,149,894 | 4/1979 | Ebihara et al. | 423/309 |
| 4,324,772 | 4/1982 | Conn et al. | 423/309 |
| 4,330,514 | 5/1982 | Nagai et al. | 423/308 |

Primary Examiner—Edward J. Meros
Assistant Examiner—Wayne A. Langel
Attorney, Agent, or Firm—Jordan and Hamburg

[57] ABSTRACT

A filler for filling in defects or hollow portions of bones to coalesce with the bone tissues is provided which comprises powders of a calcium phosphate compound having the apatite crystalline structure of each crystallite size of 400 Å or larger and of each crystal grain size of 3 μm or smaller, said calcium phosphate compound being represented by the following general formula of $Ca_m(PO_4)_nOH$ ($1.33 \leq m/n \leq 1.95$), and said powders being fluidized or plasticized.

12 Claims, 6 Drawing Figures

FILLER FOR FILLING IN DEFECTS OR HOLLOW PORTIONS OF BONES

CROSS-REFERENCE TO RELATED APPLICATION

This application is a continuation-in-part application of application Ser. No. 191,894 filed Sept. 29, 1980, abandoned.

BACKGROUND OF THE INVENTION

1. Field of the Invention

The present invention relates generally to a medical material, and particularly to an inorganic filler to be filled in defects or hollow portions formed by a removal operation of bone tumor or other causes in the bones of a living body to promote formation of new bone tissue at the filled portions and to coalesce with the bone tissue after the injured portions are completely cured.

2. Prior Art

In the surgical or orthopedic field, defects or hollow portions of bones are frequently formed by highly complicated fractures or a removal operation of bone tumor, and such defects or hollow portions should be cured by symphysis. In the prior art method, a cancellous bone is taken up from flank bones or other bones of the patient per se to be filled in the injured portion of bone to promote the cure of bone tissue. However, this prior art method is disadvantageous in that the patient suffers a greater pain from cumbersome labours necessitated in the operation, since a bone tissue other than the injured portion is taken out for use. Moreover, a sufficient amount of autoplastic bone cannot always be taken up from the patient's body for filling in a large defect or hollow portion of bone, and a certain substitute material is required to supplement the shortage of the required bone tissue in such a case.

Other than the method of autoplastic filling, there are a homogeneous bone implantation method and a heterogeneous bone implantation method. As to the homogeneous bone implantation method, uses of frozen bones and decalcified bones have been investigated but have not yet reached the stage of clinical practice. In the heterogeneous bone implantation method, a so-called keel bone, which is prepared by removing proteins from a bone of cattle, is used in some cases. However, both of these known methods are not only accompanied with foreign body reactions but also lack osteogenic capacity, so that the post-operation course is not always good. Accordingly, there is an increasing demand for an artificial filler material for filling in defects or hollow portions of bones which is excellent in compatibility with the living body and has high osteogenic capacity to promote the bone-forming reaction at the filled portion and at the vicinity thereof to accelerate curing of the structure and function of injured bone tissue.

With the aim to reducing the period of time required for curing the fractured bone, an internally fixing method is sometimes adopted wherein the fractured bone is directly fixed by the use of a metal plate, nail or screw. However, adopting such a method, there is often a case where so lengthy a time as six months or a whole year is necessary for complete curing. Furthermore, if the internally fixing method is adopted, the materials used for internal fixing should be removed from the patient's body after the fractured bone is cured, and thus the patient suffers tremendous physical, psychological and economical burdens. If a filler material of the aforementioned kind for promoting the osteogenic capacity and for accelerating the remedy or cure of the fractured or injured portion is developed, it will be made possible to attain the object of therapy for a short period of time without the application of the internally fixing method. The filler material of the aforementioned kind may be also used for the therapy of pseudoarthrosis. It is, therefore, considered that the development of such filler is of great medical value and contributes to welfare of humankind.

On the other hand, various metals and plastics materials have hitherto been used as the substitute materials for hard tissues of living body. However, these conventional materials are apt to be dissolved or deteriorated under the severe environment in the living body and are often accompanied with poisonous actions or foreign body reactions. For this reason, biomaterials of ceramics which have improved compatibilities with a living body attracted public attention in recent years. At the present time, an artificial bone, an artificial joint and an artificial radix dentis made of single crystalline or polycrystalline alumina ($Al_2O_3$) and an artificial radix dentis made of sintered calcium tertiary phosphate ($Ca_3(PO_4)_2$) or sintered hydroxyapatite ($Ca_5(PO_4)_3OH$) have been proposed. It has been reported that these materials are excellent in compatibility with a living body, for example, no appreciable formation of membrane caused by the foreign body reaction is observed when a sintered article of hydroxyapatite is implanted in a bone of a living body, which shows the direct connection between the sintered article and the bone tissue. However, these implantation materials are disadvantageously too hard and fragile, similarly as is the case of common ceramic materials, and should be improved in toughness and impact strength in order to use in the form of artificial bone or artificial radix dentis practically.

OBJECTS AND SUMMARY OF THE INVENTION

An object of the present invention is to provide a filler for filling in defects or hollow portions of bones which is excellent in compatibility with the living body and free from foreign body reaction.

Another object of the present invention is to provide a filler for filling in defects or hollow portions of bones which can facilitate formation of new bone tissue remarkably and can considerably cut down the period of time required for curing the structure and function of bone tissue.

A further object of the present invention is to provide a filler for filling in defects or hollow portions of bones which can coalesce with the bone tissue to form an integral autoplastic bone.

According to the present invention, there is provided a filler for filling in defects or hollow portions of bones to coalesce with the bone tissues, comprising powders of a calcium phosphate compound having the apatite crystalline structure of each crystallite size of 400 Å or larger and of each crystal grain size of 3 μm or smaller, said calcium phosphate compound being represented by the following general formula of:

$$Ca_m(PO_4)_nOH (1.33 \leq m/n \leq 1.95);$$

and said powders being fluidized or plasticized.

DESCRIPTION OF THE INVENTION

Various forms of calcium phosphate compounds are known including a compound referred to as hydroxyapatite and represented by the rational formula of $Ca_5(PO_4)_3OH$. A group of minerals referred to as generally apatite is represented by the rational formula of $M_m(RO_4)_nX$, wherein the site shown by M is occupied by a divalent cation such as $Ca^{2+}$, $Sr^{2+}$, $Ba^{2+}$, $Pb^{2+}$, $Zn^{2+}$, $Mg^{2+}$ and $Fe^{2+}$ or a trivalent or monovalent cation such as $Al^{3+}$, $Y^{3+}$, $La^{3+}$, $Na^+$, $K^+$ and $H^+$, the site shown by $RO_4$ is occupied by an anion such as $PO_4^{3-}$, $VO_4^{3-}$, $BO_3^{3-}$, $CrO_4^{3-}$, $SO_4^{2-}$, $CO_3^{2-}$ and $SiO_4^{4-}$ and the site shown by X is occupied by an anion such as $OH^-$, $F^-$, $Cl^-$, $O^{2-}$ and $CO_3^{2-}$. Many compounds having the resembling crystalline structures are included in this group. The aforementioned hydroxyapatite is a typical compound having the apatite crystalline structure and the composition theoretically represented by $Ca_5(PO_4)_3OH$. However, the composition of this compound produced by artificial synthesis is not always represented by the theoretical formula but is represented by the formula of $Ca_m(PO_4)_nOH$ wherein the molar ration of m/n ranges within $1.33 \leq m/n \leq 1.95$. Although many hypotheses have been presented with regard to the phenomenon of variation of the value m/n (molar ratio) in a wide range, this is considered due to the particular crystalline structure of the apatite compound. If the composition is within the range as set forth above, the aimed compound may be artificially synthesized while avoiding the intermingled presence of different phases. In the present invention, the compounds having the compositions within the range as set forth above and having the apatite structure from the crystallographical viewpoint are referred to as the calcium phosphate compounds having the apatite crystalline structures or the apatite calcium phosphate compounds which include hydroxyapatite of the theoretical composition. The calcium phosphate compounds represented by the formula of $Ca_m(PO_4)_nOH$ are readily modified by incorporating various different ions at the sites of Ca, $PO_4$ and OH. It is to be noted here that the compounds used in the present invention include such modifications modified by the presence of any different ions so far as the compatibility with the living body is not lost and the composition range of m/n is maintained within $1.33 \leq m/n \leq 1.95$.

The crystallite size of the apatite calcium phosphate compound used in the present invention should be 400 Å or larger, while the crystal grain size of the same compound should be 3 μm or smaller. The "crystallite size" used herein is obtained and calculated from X-ray diffraction patterns, whereas the "crystal grain size" is directly measured from an electron microscope, as will be described in detail hereinafter. The crystallite size or crystal grain size of the hydroxyapatite forming the hard tissue of the living body ranges from several hundreds to several thousands Å. It is desirous that the crystallite size or crystal grain size of the powders used in the filler of the present invention approximates the crystallite size or crystal grain size of the hydroxyapatite constituting the living body in order to promote formation of new bones at the vicinity of particles of the filler filled in the defects or hollow portions and to form a uniform living tissue as the result of the coalescence between the new bones and the particles of the filler. If the crystal grain size of the apatite calcium phosphate compound exceeds 3 μm, the formation of new bones is retarded resulting in delayed curing of the defects and further the newly formed bones lack uniformity. There are also cases where foreign body reactions are observed if the crystal grain size of more than 3 μm is used. On the contrary, if the crystallite size is less than 400 Å, the filler particles in the new bone are less crystallizable so that the coalescing capacity thereof does not reach the satisfactory level.

It is preferred that the particle size distribution of the apatite calcium phosphate compound used in the present invention is such that powders each having the particle size of 300 μm or less, preferably 150 μm or less occupy 70% or more of the total weight. If the content of particles having the particle size of 300 microns of less does not reach 70% by weight, when the filler is added with water or an isotonic sodium chloride solution to be fluidized or plasticized, the particles tend to separate from water. As a result, there is a fear that the filler cannot be plasticized or the particles are sedimented only to the lower portion of the hollow portion to result in formation of unfilled vacancy at the top portion when the filler is filled in the living body. As far as the particle size distribution is within the range as aforementioned, the presence of some quantities of larger particles having the particle size of about several mm may be allowed.

Natural materials, for example, bone ashes prepared by baking bones of animals may be used as the apatite calcium phophate compound of the present invention, and synthetic materials prepared by the known wet process, dry process and hydrothermal process may also be used for the same purpose. The apatite calcium phosphate having a composition within the range as defined above and synthesized by the wet process is generally obtained in the form of precipitate composed of minute particles while being somewhat altered depending on the temperature and other conditions at the synthesis step, and may be separated from the solvent by means of filtration or centrifugal separation and then dried at a temperature of lower than 700° C. followed by pulverization to form a material of impalpable powder. This powder form material may be directly fluidized or plasticized, as will be described hereinafter, to be filled in defects or hollow portions of bones as a filler having the osteogenic capacity. However, the aforementioned material prepared by the wet process is preferably baked at a temperature ranging within 700° C. to 1250° C., preferably 700° to 1100° C., optionally subjected to a pulverization treatment to form a powdered material, and then fluidized or plasticized for use as a filler for filling in defects of hollow portions of bones, in order to improve the crystallinity of the particles and to sufficiently sterilize by heating for preventing infection by bacteria and for preventing foreign body reaction caused by organic materials. Baking effected at a temperature of not higher than 700° C. is unsatisfactory, since no appreciable growth of crystals takes place. As the baking temperature is raised to higher than 1250° C., growth of crystal grain becomes somewhat excessive, thus being unsatisfactory.

An apatite calcium phosphate compound having a relatively coarse crystal grain size is prepared by the dry process or by the hydrothermal synthesis process. In the case where lumps are included, such lumps are crushed to obtain powders or particles. If these powders or particles are heated again at a temperature of lower than 1250° C. to be sterilized, they can be smoothly filled in defects or hollow portions of bones to fulfill their functions as the filler.

The calcium phosphate compound used in the present invention has preferably a calcium ion concentration of from 3 to 5 ppm and a phosphoric ion concentration of from 1 to 4 ppm when dissolved into an isotonic sodium chloride solution and measured after 1 to 72 hours. If the ion concentrations of $Ca^{2+}$ and $PO_4^{3-}$ are out of the ranges above defined, that is if the calcium phosphate compound is rather insoluble or soluble it is not possible to enhance the remarkably rapid growth of new bones. It is understood that appropriate solubilities of $Ca^{2+}$ and $PO_4^{3-}$ of the filler into body fluid with the lapse of time will greatly enhance the rapid growth of new bones.

The powders prepared by any of the aforementioned synthesis processes and/or the particles obtained by baking the powders are fluidized or plasticized by the addition of a liquid, such as water or an isotonic sodium chloride solution, and then filled in the defects or hollow portions of bones. By fluidizing or plasticizing the powders or particles, the fine powders are prevented from scattering to adhere to undesired portions of the patient's body other than the injured portion so that any adverse influence caused by adherence of scattering powders is excluded. Another advantage attained by the use of a fluidized or plasticized filler is that the defects or hollow portions of bones are wholly and uniformly filled with the filler by a simple injection operation. The quantity of the liquid to be added is varied depending on the particle size of the used filler and the presence or absence of pores. If water or an isotonic sodium chloride solution is used, the added quantity thereof may be determined within the range in which separation of water does not occur and the powders or particles are sufficiently plasticized to be easily filled in the hollow portions. In general cases, 0.1 to 2 parts by weight of water or an isotonic sodium chloride solution is added to 1 part by weight of the filler.

The aforementioned powders or particles may be put into a granulator, for example a rolling granulating machine, and added with a liquid, such as water or isotonic sodium chloride solution, to form granules. A preferred shape of granules is spherical or pilular to facilitate filling, and the diameter of granules may be varied depending on the dimensions of defects or hollow portions in which the granular filler is filled. These granules may be stored in a container, such as a glass bottle, with a seal and poured into the injured portion when in use. By the use of the granular filler, the hollow portion can be uniformly filled with such granules with voids left therebetween. If dense filling is desired, the granules may be simply pushed into the hollow portion using a bar or like implement since the granules are plastic. This plastic granules have advantages that they can be easily handled when in use and that the filling density may be controlled as desired.

The aforementioned granules or the dry powders may be baked at 700° to 1250° C., preferably 700° to 1100° C. to form baked beads. The baking temperature is limited as aforementioned for the same reason described hereinbefore in the case of baking the powders. If baked above 1250° C., the sintering proceeds too excessively to result in the formation of sintered beads having smaller porosity. Thus, the living tissue cannot sufficiently penetrate into the pores. Since the baked beads are porous, the living tissue is allowed to penetrate into the pores, so that formation of new bone at the vicinity of particles forming the sintered bead is remarkably promoted and the baked material coalesces with the new bone rapidly. Further, since the baked material is in the form of baked beads, there is no fear of being scattered when filing in the injured portion without any adverse affect due to the adherence of powders to other portions. These baked beads are preferably spherical, so that they are fluent nevertheless individual beads are solid. Therefore, it may be said that these baked beads can be fluidized, as referred to in the present invention, to be poured into the injured portion to fill the same easily and immediately. Moreover, the particle size of these beads can be freely adjusted at the bead formation step. If the particle size distribution is controlled in a narrow range, the injured portion of bone can be filled at low density with increased voids. On the contrary, if the particles size distribution is spread and beads having different diameters are included, relatively high density filling may be realized.

The aforementioned porous baked beads may be used in the dry state as they are, since they are fluent as mentioned hereinabove. However, the porous baked beads may be added to the powder form filler and then added and kneaded with liquid such as water or an isotonic sodium chloride solution for use in the form of a paste. If the porous beads are mixed in the paste, the porosity of the entire paste can be increased. The baked beads may be added in a ratio at which the fluidity or plasticity of the filler of paste form is not lost, and the preferred ratio being 30% by weight or less based on the total weight of the paste.

As the filler for filling in defects of bones according to the invention, the aforementioned apatite calcium phosphate compound may be used singly. However, it is preferred that a cancellous bone obtained by crushing a bone may be mixed together to further increase the bone formation speed. The cancellous bone of autoplastic origin has been conventionally used singly as a filler for filling in a defect of bone. However, there is often a case where a sufficient quantity of cancellous bone enough for filling the defect cannot be taken up, or it is desired that the quantity of cancellous bone of autoplastic origin is reduced as small as possible. The apatite calcium phosphate compound of the present invention may be mixed at a desired ratio with the autoplastically obtained cancellous bone. On the other hand, a bone of foreign origin has hitherto been limitedly used singly so as to avoid the foreign body reaction or other problems. However, when the bone of foreign origin is mixed with the apatite calcium phosphate compound of the present invention, the adverse reactions including the foreign body reaction can be considerably reduced to facilitate therapy. The mixing ratio of bone of foreign origin is preferably less than 50% by weight of the total weight, and a particularly preferable mixing ratio is less than 20% by weight. If more than 50% by weight of bone of foreign origin is mixed, reduction in adverse reaction becomes unsatisfactory nevertheless the bone formation speed is increased. Similarly as in the case where the apatite calcium phosphate compound is used singly, the mixture of the compound and the cancellous bone may be added with water or an isotonic sodium chloride solution to be fluidized or plasticized to prepare a filler to be filled in a defect of bone.

The filler of the invention having the construction as aforementioned, has the fluidity or plasticity so that it can be uniformly and wholly filled in any defects or hollow portions of bones irrespective of how complexly shaped they are. Furthermore, the filler of the invention is different from the conventional implant materials made of integral articles in that it is made of powders, which are added in a fluidized or plasticized state prior to filling in an injured portion of bone, so that the powders are diffused in the implanted living body uniformly and the surfaces of the powders are readily covered with the growing tissue. More specifically, when the filler of the invention is filled in a defect or hollow portion of bone, new granulation tissues surround the particles after the lapse of a short period of time and the particles are present while being dispersed in the granulation tissues. It should be noted here that no giant cells caused by foreign bodies appear at all, since the powders of the present invention made of the apatite calcium phosphate compound having crystallite size of 400 Å or larger and crystal grain size of 3 μm or smaller have remarkably improved compatibilities with the living tissues. Under such condition, osteoid with attendant osteoblast adheres to the peripheral portions of the particles without forming membranes caused by foreign bodies, and new bone tissues are rapidly formed from the peripheral surfaces of the particles towards their vicinities and the granulation tissues are changed to the connection tissues with the lapse of time. The filler of the invention composed of powders or baked beads has a large surface area since the former is in powder form while the latter is porous. The filler in such forms, therefore, increases the new bone formation speed considerably. The new bone tissues formed on the surfaces of the particles continue to grow and cross-link the particles which are present by close spacings. As the cross-linking structures grow, new cancellous bones are formed here and there and finally all of the filler particles are connected with each other by the newly formed dense cancellous bone integrally. As a result, an integral structure is formed, where powder particles of the apatite calcium phosphate compound are dispersed in a newly formed bone beam which has a low calcium density. Then, the new bond becomes denser to form a new bone tissue having the same composition as that of the surrounding old bone for covering the defect or hollow portion of bone. Finally, the injured portion is completely cured without any appreciable differnce, as the particles of the filler assimilate with the new bone. However, formation of bone tissue stimulated by the filler of the invention does not proceed too far beyond the functional requirement generally required for normal bone tissue. In this connection, the filler of the invention has another advantage in that the portions thereof filled in the unnecessary portions are absorbed in the living body. As has been mentioned hereinabove, new bone tissues are initially formed on the surfaces of the particles of the filler. Accordingly, it is preferred that the specific surface area of the particles is increased and a larger number of particles is present in a unit volume, in order to increase the bone formation speed. Also, the spacings between the particles should be preferably closer at some extent for allowing the new bone to cross-link the particles to form a bone beam and further to connect the entire structure to form a cancellous bone. The speed of assimilation is accelerated as the particle size is smaller, since the compound is assimilated with the newly formed bone from the surfaces of the particles toward the inner portions thereof. In view of the foregoing, smaller particles are preferred to increase the bone formation speed. However, since osteogenic materials will be fed from the living body inbetween the particles, the particle size is spontaneously limited and the lower limit of the particle size is determined by the supply of the osteogenic materials.

As will be clearly understood from the foregoing description with regard to the construction, action and function of the present invention, the present invention is entirely different from the conventional technical concept of providing substitute materials for hard tissues including artificial bones and artificial radix dentis which are made of sintered single crystalline alumina (sapphire), sintered polycrystalline alumina or sintered hydroxyapatite and developed with the aim to simply avoiding the foreign body reaction between the bone tissue and to improving the adherence property. In other words, the filler of the present invention promotes the regeneration or self-curing action of the patient's bone tissue of itself taking place at the defects or hollow portions of bones, and the filler composition per se is incorporated into the bone tissue and coalesces therewith. For this reason, the inherent strength of the material used in the present invention is out of the question.

Although an appreciable effect can be obtained only by filling the filler of the invention in the defects or hollow portions of bones, formation of new bone will be further promoted if a portion of the filler reaches the bone marrow cavity. New bones are initially formed at the portions of defects where the filler particles contact with the bone marrow and then gradually grow into the hollow portions. However, the newly formed bone tissue formed in the bone marrow cavity and essentially to be discarded ultimately is absorbed in the living body by the action of osteoblasts, and the requisite amount of new bone is left only at the necessary portion. According to this method, it is possible to ensure curing and to shorten the time required for therapy. The filler according to the invention exhibits its function only when it is used under the environment of living body where the bone tissue is to be formed, in other words only when it is used at the defects or hollow portions of bones. The result of the experiment, where the filler of the invention is injected into the femoral muscle tissue of a rabbit, reveals no sign of bone formation in the muscle tissue after all.

As has been described in detail hereinbefore, the powder or particle form apatite calcium phosphate compound according to the invention has a remarkably improved compatibility or adaptability with the living tissues and also has an excellent osteogenic capacity. Moreover, the filler of the invention is advantageous in that it coalesces with the bone tissue to be incorporated thereinto and exhibits a synergistic action to promote the regeneration or self-curing function of the bone tissue per se remarkably. The filler of the invention is used in a simple manner and the materials for the filler can be supplied from inexhaustible sources to make it possible to supplement the shortage in supply of autoplastic bone.

The filler of the invention can be used not only for filling in defects or hollow portions of bones to remedy the bone tumor or the fractured bone and in the arthroplasty operation, the spinal fusion operation and the intervertebral disk fusion operation, but also for filling in the injured portion formed in the processus alveolaris caused by pyorrhea alveolaris.

EXAMPLES OF THE INVENTION

The present invention will now be described more specifically by referring to several examples thereof. However, it should be appreciated that the present invention is not limited only to the examples given below.

Throughout the specification and appended claims, the crystallite size of the calcium phosphate compound having the apatite crystalline structure will be indicated by the value of each crystallite in the direction of a-axis obtained from the half-width of the peak of diffraction measured by the X-ray diffractiometry wherein the spacing (200) is $2\theta = 21.8°$, when the crystallite size is less than 0.1 $\mu$m; and the crystal grain size will be indicated by the practically measured average diameters of the crystal grains measured by using a scanning electron microscope, when the crystal grain size is more than 0.1 $\mu$m.

EXAMPLE 1

An apatite calcium phosphate compound (Molar Ratio of Ca/P=1.65) was synthesized by the wet process wherein phosphoric acid was dropwise added into a solution of calcium hydroxide. The dried powders of this compound were baked at 850° C. for 5 hours. The size or dimensions of crystallites was measured by the X-ray diffractiometry to reveal that the average diameter of crystallite along the c-axis was about 600 Å and the average diameter of crystallite along the a-axis was about 500 Å. Coarser powders were removed such that all particles pass through a net of 300-micron meshes. The thus obtained powders were added with an isotonic sodium chloride solution to form a paste which was injected into the bone-marrow of the femur of a rabbit. The injected portion was kept observed. Formation of new bones in the neighbourhood of the injected powders was observed after only one week from the time of injecting the paste of the apatite calcium phosphate compound, and no appreciable sign of foreign body reaction was observed at all. Then, the formed new bones were rapidly grown and it was observed that the particles composed of said compound were entirely incorporated into the newly growing bones and coalesced with the bone tissue. As will be apparent from the foregoing, the powders composed of said compound exhibits a remarkable osteogenic capacity which may be deemed as the particular effect of the apatite calcium phosphate compound when compared to the result of a similar comparative experiment wherein powders of alumina were used.

EXAMPLE 2

Each of the powders of the compounds synthesized by the wet processes and each having the ratio of m/n of 1.38, 1.56, 1.73 and 1.89 was baked at 850° C. for 2 hours. The crystal grain sizes of these samples determined by measuring the diameters of crystallites by means of the X-ray diffractiometry were as follows:

| m/n | Average Diameter along the c-Axis | Average Diameter along the a-Axis |
|---|---|---|
| 1.38 | 580 Å | 400 Å |
| 1.56 | 640 Å | 450 Å |
| 1.73 | 720 Å | 520 Å |
| 1.89 | 800 Å | 600 Å |

Every baked powder was screened to obtain sample powders of less than 149 microns in size. Every powder was subjected to the X-ray diffractiometry to ascertain that all of these powders showed the diffraction pattern of hydroxyapatite and did not contain any other compounds. In accordance with the general procedure as set forth in Example 1, each of the powders was injected into the bone-marrow of the femur of a rabbit, and the formation of new bone at the injected portion was observed to ascertain that the function of each of these powders on the formation of bone tissue was equivalent to that observed in Example 1.

As has been described hereinbefore, the compositions of the apatite calcium phosphate compounds artificially synthesized are not always represented by the theoretical rational formula of $Ca_5(PO_4)_3OH$, but may be represented by the general formula of $Ca_m(PO_4)_nOH$ wherein the ratio of m/n, i.e. the molar ratio of Ca to P, varies within the range of from 1.33 to 1.95. In the present invention, all such compounds having the compositions as mentioned above are inclusively referred to as apatite calcium phosphate compound. When reviewing the results of this Example, it will be reasonably seen that every such compound having the compositions as defined above exhibits similar effects to those obtained in the animal experiment shown in Example 1.

EXAMPLE 3

A. Clinical Tests

The powders used in Example 1 and composed of the apatite calcium phosphate compound having the molar ratio of m/n=1.65 and synthesized by the wet process were sufficiently dried followed by being pulverized, and then screened to obtain a sample which passed a net of 149-micron meshes. The dried and screened powders were baked for two hours at 300° C., 500° C., 700° C., 1000° C., 1250° C. and 1350° C., respectively. Each of the sample powders thus made was fluidized by adding an isotonic sodium chloride solution thereto. The fluidized sample powders baked at respective temperatures were filled in defects (2 mm$\phi$) artificially made in cortical bones of the femurs of rabbits. After four weeks, each rabbit was killed and the femur was cut out. The dyed specimens were prepared from every killed rabbit after being decalcified and were observed.

The results of the observations showed that in the cases where the sample powders baked at 700° C., 1000°

C. and 1250° C. were applied, osteoblasts were observed in the vicinity of the filled powders and that the surfaces of all the sample powders were covered with new bones. It was also observed that there were a lot of portions where thick bone beams were connected between the sample powders and that there were not any giant cells caused by foreign body reactions.

In the case where the sample powders baked at 300° C. were applied, the formation of new bones was observed only a little and there were observed many giant cells caused by foreign body reactions.

In the cases where the sample powders baked at 500° C. and 1350° C. were used, respectively, it was observed that the formation of new bones was far smaller than those in the cases where the sample powders baked at 700° C. to 1250° C. were used although giant cells caused by foreign body reactions were not observed.

B. Structure

X-ray diffraction patterns of hydroxyapatite powders baked at respective temperatures given above were determined, using a x-ray diffraction device available under the trade name "ROTAFLEX" produced by Rigaku Denki K.K.

The conditions for the determination were as follows:

| Target | Cu |
|---|---|
| Voltage, Current | 40 KV, 100 mA |
| Count Full Scale | 4000 cps |
| Time Constant | 0.5 sec |
| Scanning Speed | 4°/min |
| Divergency | 1° |
| Receiving Slit | 0.15 mm |

Figure 6:
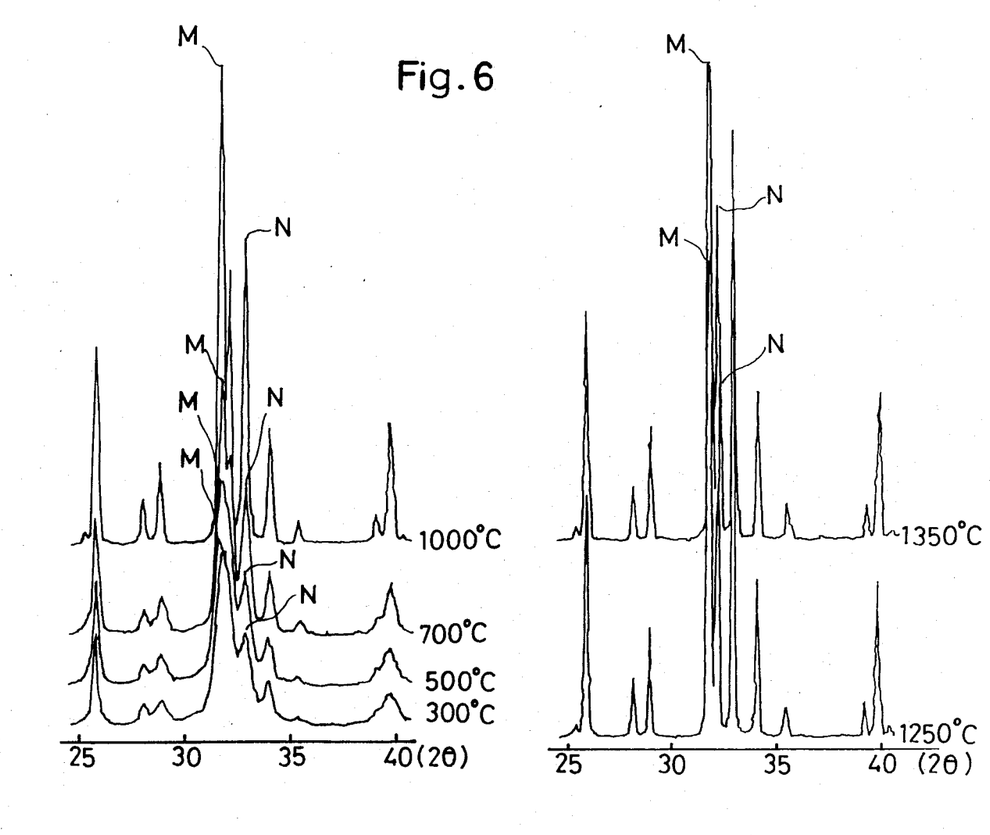
FIG. 6 shows X-ray diffraction patterns of hydroxyapatite powders baked at various temperatures.

The x-ray diffraction patterns thus determined are shown in FIG. 6. As can be seen from FIG. 6, it will be noted that diffraction lines at 31.8° (Peak M) and at 32.2° (Peak N), which were obtained from hydroxyapatite powders baked at 300° C. and 500° C., respectively, are not completely separate but rather integral. On the other hand, a diffraction line obtained from hydroxyapatite powders baked at 700° C. shows appreciable separation between the peaks M and N. At higher temperatures, completely separate peaks are observed. From the fact, it is noted that when baking is effected at a temperature of 700° C. or higher, amorphous hydroxyapatite is changed to have a crystalline structure.

In view of the clinical test results above showing that particularly remarkable formation of new bones were observed by the use of the powders baked at a temperature of from 700° C. to 1250° C. as compared with those baked at 500° C. or lower, it is understood that crystalline hydroxyapatite obtained by baking at 700° C. or higher exhibits remarkable formation of new bones.

C. Size of Crystallite and Crystal Grain Size

(1) Size of Crystallite

The sizes of hydroxyapatite crystallite along the a axis and c axis were measured with reference to [200] diffraction line (a-axis, $2\theta = 21.8°$) and [002] diffraction line (c-axis, $2\theta = 25.9°$) obtained from the x-ray diffraction patterns. The sizes of crystallite were calculated by the Scherrer Method in accordance with the following equation:

$$D = K\lambda/\beta \cos\theta$$

(wherein D stands for the size of crystallite, $\lambda$ for wave length of x-ray, K for pattern coefficient (1.0 was used here), and $\beta$ for width of diffraction line.)

$\beta$ was determined by the half width method. The conditions were as follows:

| Target | Cu |
|---|---|
| Voltage, Current | 40 KV, 100 mA |
| Count Full Scale | 800 or 2000 cps |
| Time Constant | 5 sec |
| Scanning Speed | ¼°/min |
| Divergency | 1° |
| Receiving Slit | 0.15 mm |

The results are shown in Table 1 below:

TABLE 1

| Baking Temp. (°C.) | a axis (Å) | c axis (Å) |
|---|---|---|
| 300 | 180 | 440 |
| 500 | 190 | 480 |
| 700 | 410 | 650 |
| 1000 | Above 2000 | Above 2000 |
| 1250 | " | " |
| 1350 | " | " |

From Table 1, hydroxyapatite powders baked at 700° C. show abrupt increase in sizes along both a and c axes as compared with those baked at 500° C. or lower. Considering the clinical test results above, it is understood that the hydroxyapatite powders baked at 500° C. and 300° C. have too small crystallite size to form new bones rapidly, whereas those baked at 700° C. or higher have appropriate crystallite size for the rapid growth of new bones.

(2) Crystal Grain Size

Crystal grain sizes of hydroxyapatite powders baked at 1000° C. or higher were measured by means of a scanning type electron microscope. In this connection, it is to be noted that by means of x-ray diffraction patterns it is impossible to measure crystal grain size of hydroxyapatite powders baked at 1000° C. or higher since such powders are calculated to have the sizes of above 2000 Å because of difference in order. (See Table 1 above.)

Three photographs of hydroxyapatite powders baked at 1000° C., 1250° C. and 1350° C. were taken, respectively, through the electron microscope. The average crystal grain size of the powders was directly calculated from the three photographs, respectively. The results are shown in Table 2 below:

TABLE 2

| Baking Temp. (°C.) | Average Crystal Grain Size (μm) |
|---|---|
| 1000 | 0.3 |
| 1250 | 2.2 |
| 1350 | 4.9 |

From Table 2 above, it is noted that hydroxyapatite powders baked at 1350° C. have an average crystal grain size of 4.9 μm, whereas those baked at 1250° C. have 2.2 μm. This shows an abrupt increase in crystal grain size at 1350° C. Referring to the clinical test results above, it is understood that the hydroxyapatite powders baked at 1350° C. has too large crystal grain size to form new bones rapidly, while those baked at 1250° C. or lower have appropriate crystal grain size for the rapid growth of new bones.

D. Solubility

Porous hydroxyapatite bodies were prepared by impregnating a hydroxyapatite slurry into pores of substrate bodies of an organic material followed by baking to burn away the organic material. Baking was effected for an hour at a temperature of 300° C., 500° C., 700° C., 1000° C., 1250° C. and 1350° C., respectively.

The porous bodies thus formed were subjected to solubility tests. One part by weight of each porous body baked at different temperatures described above was impregnated into 100 parts by weight of an isotonic sodium chloride solution maintained at 37° C. and oscillated for 1, 3, 6, 12, 24 and 72 hours, respectively to measure ion concentrations of $Ca^{2+}$ and $PO_4^{3-}$ dissolved into an isotonic sodium chloride solution after respective oscillation hours.

The concentration of $Ca^{2+}$ was measured by the atomic absorption method and that of $PO_4^{3-}$ was measured by the molybdenum blue absorptiometric method. The results are shown in Table 3 below:

TABLE 3

| Ion | Baking Temp. (°C.) | Ion concentration (ppm) Oscillation hours (hr.) | | | | | |
|---|---|---|---|---|---|---|---|
| | | 1 | 3 | 6 | 12 | 24 | 72 |
| $Ca^{2+}$ | 300 | 11.1 | 10.6 | 11.2 | 11.1 | 10.9 | 13.1 |
| | 500 | 9.7 | 8.9 | 9.3 | 9.4 | 9.9 | 10.4 |
| | 700 | 4.8 | 4.4 | 4.3 | 4.5 | 4.8 | 5.0 |
| | 1000 | 3.0 | 3.1 | 2.9 | 3.0 | 2.8 | 2.8 |
| | 1250 | 3.1 | 3.1 | 3.1 | 2.8 | 2.9 | 2.9 |
| | 1350 | 5.4 | 5.9 | 5.9 | 6.6 | 6.4 | 6.0 |
| $PO_4^{3-}$ | 300 | 13.5 | 13.6 | 13.9 | 12.6 | 10.7 | 11.0 |
| | 500 | 5.8 | 4.7 | 5.4 | 4.4 | 5.0 | 4.3 |
| | 700 | 3.9 | 3.6 | 3.1 | 3.7 | 3.1 | 3.3 |
| | 1000 | 1.6 | 2.3 | 1.6 | 1.2 | 0.9 | 1.1 |
| | 1250 | 3.9 | 4.0 | 3.6 | 3.1 | 2.8 | 2.7 |
| | 1350 | 5.1 | 5.5 | 4.3 | 3.9 | 4.5 | 3.6 |

It is noted from Table 3 that porous bodies baked at 700° C. to 1250° C. have smaller solubilities than those sintered at 500° C. or lower and at 1350° C. with respect to both $Ca^{2+}$ and $PO_4^{3-}$. Referring to the clinical test results above, it is understood that the powders baked at 500° C. or lower and at 1350° C. are too soluble to enhance the rapid growth of new bones, while those baked at 700° C. to 1250° C. have appropriate solubilities to form new bones rapidly.

EXAMPLE 4

740 g of calcium hydroxide (a special grade chemical reagent produced by Junsei Kagaku K.K.) was suspended in 20 liters of water. An about 30 wt% phosphoric acid solution (prepared by diluting a special grade chemical reagent produced by Wako Junyaku K.K.) was dropwise added to the suspension while agitating the suspension and maintained at 40° C. until the pH value of the liquid reached 8.8. Agitation was continued for additional one hour, and then the suspension was allowed to stand stationarily at 40° C. for 48 hours to age the same. A precipitate of apatite calcium phosphate was obtained. This precipitate was filtered by the use of a suction filter, rinsed and then dried in a hot air circulation drier maintained at 105° C. for 24 hours to form a cake which was pulverized in a ceramic pot mill to obtain dried powders having the particle size passing through a net of 300-micron meshes. Then, the powders were baked in an electric furnace maintained at 800° C. for 6 hours. The crystallite size of the baked powders was measured by the X-ray diffractiometry to find that the diameter of crystallite along the C-axis was about 550 Å and that of the a-axis was about 470 Å. After cooling outside of the furnace, the baked powders were screened using a net of 149-micron meshes to remove coarser particles and sterilized by heating again at 800° C. for one hour in the electric furnace. A baked powder sample to be used in an animal experiment was thus prepared and sealed in a clean glass ampoule.

The powder sample was subjected to the X-ray diffractiometry to ascertain that the sample was composed of the hydroxyapatite crystalline and no other compound was contained therein, and also subjected to a chemical analysis to find that the molar ratio of Ca to P, namely the ratio of m/n, was 1.67 which was coincident with the theoretical composition of a hydroxyapatite compound represented by $Ca_5(PO_4)_3OH$.

Rabbits each having the weight of about 4 kg were selected as the animals used in the following animal experiment. Under intravenous anaesthesia two holes each having a diameter of about 3 mm were drilled through the femur of each rabbit by a spacing of 15 mm. A paste prepared by adding 10 g of said powder with 8 ml of an isotonic sodium chloride solution was injected into the bone marrow space between the two holes. The rabbits were killed from one week to six months after implantation, and after labelling with tetracycline, the femurs were cut crosswise at the portion intermediate of the two holes. The decalcified and undecalcified specimens were prepared from every killed rabbit, and the histological changes of these specimens were observed.

Figure 1:
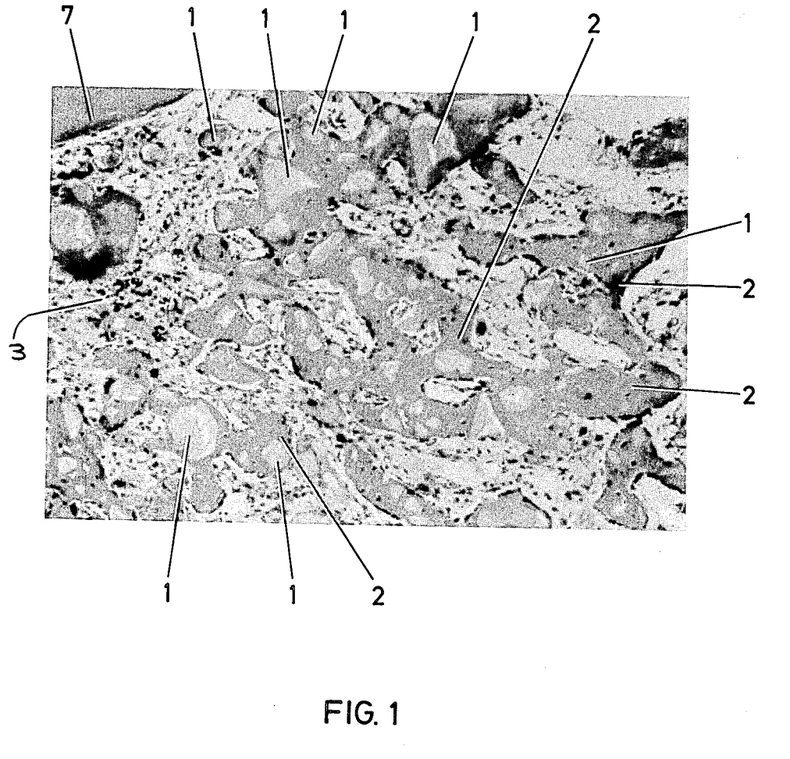
FIG. 1 is a microphotograph of a crosswise section of a decalcified specimen showing the femur of a rabbit provided with a hole filled with the filler of the invention, the femur being taken out of the rabbit killed after the lapse of one week from the time of the implantation.

FIG. 1 is a microphotograph (about 200 magnifications) of a crosswise section of the decalcified specimen showing the portion injected with the paste and taken out of the rabbit after one week from the time of implantation.

As will be apparent from the Figure, particles 1 of the apatite calcium phosphate compound are scattered in the young granulation tissue 3, and the osteoid with attendant osteoblast adhered to the peripheral portions of the particles 1. New cancellous bones 2 are formed at the portions where the particles 1 are relatively closer and these newly formed bones crosslink the particles. No giant cells caused by foreign bodies are observed at all. It should be a distinguishing feature that the newly formed bones contact the peripheries of the particles 1 of the apatite calcium phosphate compound without forming any foreign body membrane. This shows that the compound has a remarkably improved compatibility with the living body and a considerably high osteogenic capacity. In the Figure, reference numeral 7 designates the cortical bone.

After four weeks from the time of implantation, all particles of the apatite calcium phosphate compound are connected with each other through the new bones and form an integral and dense body of cancellous bone.

Figure 2:
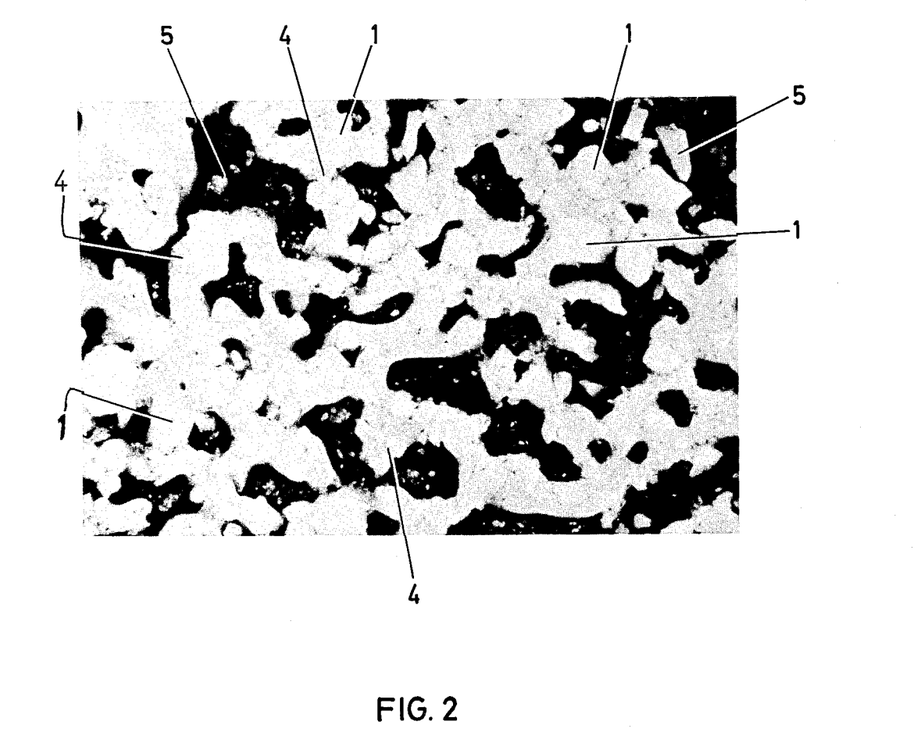
FIG. 2 is a microphotograph similar to FIG. 1, but showing the femur which is taken out of the rabbit killed after the lapse of four weeks from the time of the implantation.

FIG. 2 is a microradiographical photograph (about 200 magnifications) of a crosswise section of the undecalcified specimen showing the portion injected with the paste containing the particles of the apatite calcium phosphate compound and taken out of the rabbit after four weeks from the time of implantation. It is shown that high density particles 1 of the apatite calcium phosphate compound are scatteringly present in a low density new bone beam 4 and that the spacing between the new cancellous bones are filled with the bone-marrow tissue 5. It is also observed that the new bone is formed rapidly without being accompanied with any foreign body reaction and that all of the injected particles 1 are incorporated into the newly formed bone beam 4 and interconnected with each other.

Figure 3:
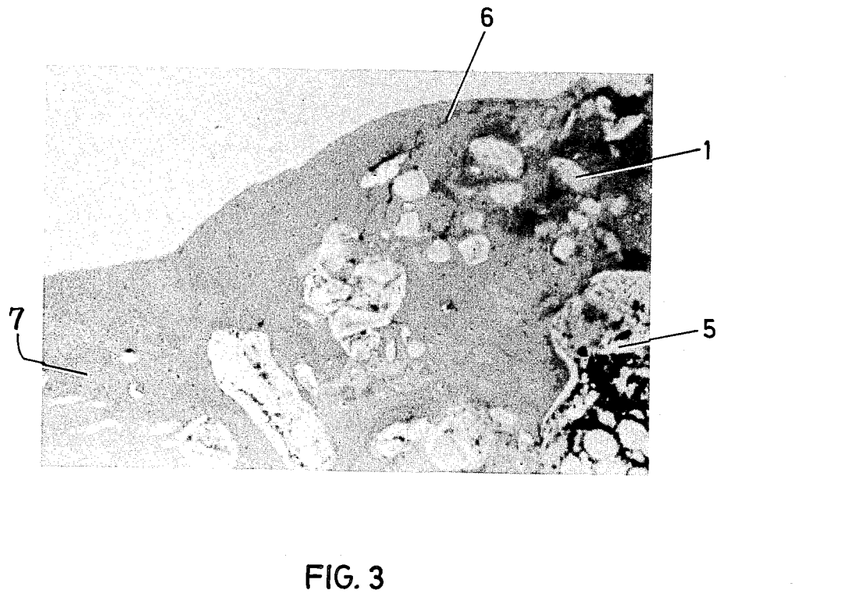
FIG. 3 is a microphotograph similar to FIG. 1, but showing the femur which is taken out of the rabbit killed after the lapse of three months.

FIG. 3 is a microphotograph (about 400 magnifications) of the decalcified specimen showing the drilled portion of the femur of the rabbit taken out of the rabbit after 3 months from the time of implantation. The drilled portion, i.e. the artificially formed defect of bone in the femur (cortical bone) is completely repaired with the new cortical bone 6 and the drilled portion forms an integral body with the surrounding original femur (cortical bone 7). Although scattering particles 1 are observed at the newly formed bone portion, no foreign body reaction is observed to show excellent compatibility of the filler with the living body. It is also observed that yound bone-marrow tissue 5 is present in the bone-marrow cavity. It is further shown that the bone-marrow tissue at that portion is refreshed and becomes rejuvenated by the injection of the paste of the apatite calcium phosphate compound.

Although bone formation is observed at some portions even after six months after the implantation, the absorption of bone prevails in the bone-marrow cavity and the cancellous bone beams are reduced in number as a whole and become coarser. On the other hand, the new bone formed at the drilled portion is changed to the cortical bone to coalesce with the surrounding original femur. This shows that formation of new bone in the defect and in the bone-marrow cavity does not continued unlimitedly but is adapted for the functional demand of the living body ultimately. In view of this fact, the filler of the invention should be appreciated to be an ideal filler material.

EXAMPLE 5

A calcium phosphate compound synthesized by the wet process was dehydrated and dried to form a cake which was baked at 1000° C. for 2 hours. The crystal grain size was measured by a scanning electron microscope to find that the average crystal grain size was 0.2 $\mu$m, the minimum crystal grain size was 0.1 $\mu$m and the maximum crystal grain size was 0.4 $\mu$m. This cake was pulverized in a ceramic pot mill to obtain a powder sample which passed a net of 149 $\mu$m meshes. The powder sample was subject to the X-ray diffractiometry to ascertain that the sample was composed of the crystalline hydroxyapatite and no other compound was contained therein, and also subjected to a chemical analysis to find that the molar ratio of Ca/P was 1.63. This powder sample was heated again at 700° C. for 5 hours to be sterilized. A powder sample to be used in an animal experiment was thus prepared and sealed in a clean glass ampoule.

A portion of the cortical bone of the femur of an adult rabbit having the weight of about 4 kg was removed to form artificially a defect of about 2 mm×5 mm. One part by weight of cancellous bone taken up from the rabbit per se was mixed with one part by weight of the powder of said apatite calcium phosphate compound, and 0.3 part by weight of distilled water was additionally added and kneaded to be plasticized. The plasticized mixture was filled in said defect formed in the bone. The same operations were performed on a group of rabbits which were killed one after another. The portion of the femur containing the defect was cut crosswise to prepare a histological specimen therefrom, and the histological change was observed.

After one week from the operation, appreciable formation of new bones was observed in the neighbourhood of the particles of the apatite calcium phosphate compound, and the particles of the apatite calcium phosphate compound and the autoplastically implanted bone pieces were interconnected with each other by the crosslinking structure of said new bones without any foreign body reaction occurring. After four weeks, considerable development of growth of a new bone beam was observed, and all of the particles of the apatite calcium phosphate compound and the cancellous bone pieces were interconnected by the new bone beams, whereby the portion filled with the filler was made of the cancellous bone tissue in its entirety. After 3 months from the operation, it was observed that said cancellous bone tissue was changed to the cortical bone tissue to coalesce with the surrounding original femur so that the artificially formed defect of bone was completely repaired. This result shows that the shortage is autoplastically taken-up bone may be supplemented with powders of calcium phosphate compound having the apatite crystalline structure to be filled in a defect of bone, whereby the object of therapy can be attained for a shorter period of time according to the present invention.

COMPARATIVE EXAMPLE 1

A high purity alumina powder produced by Iwatani Kagaku K.K. (Trade Name: RA-30, $Al_2O_3=99.9\%$, 100% passing through a net of 149 $\mu$m meshes) was used. Following a similar procedure as in the preceding Examples, a paste was prepared from said alumina powder which was injected into the bone-marrow cavity of the femur of a group of rabbits. The progress of new bone formation was investigated.

Figure 4:
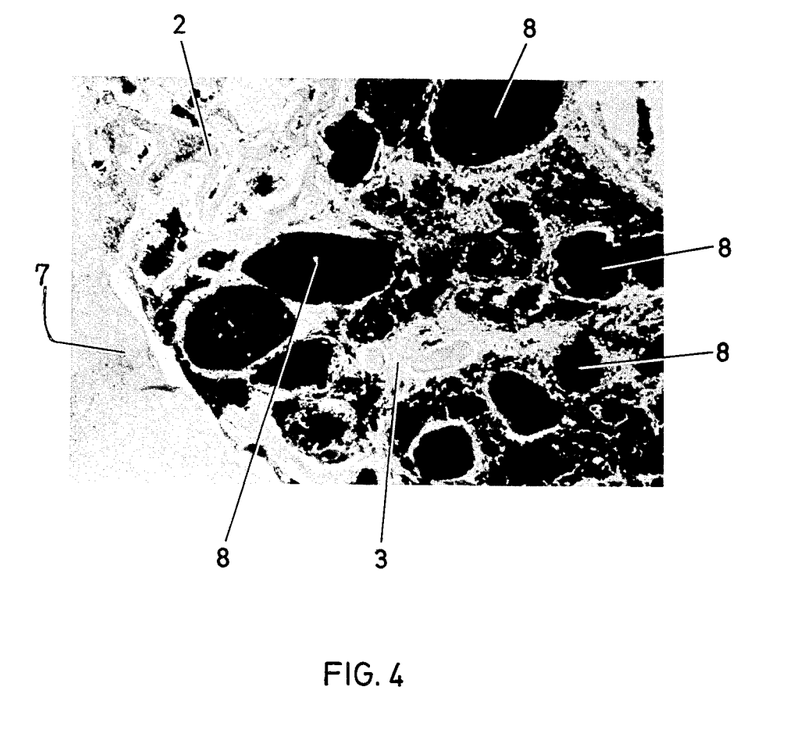
FIG. 4 is a microphotograph similar to FIG. 1, but showing the femur having a hole filled with an alumina powder in place of the filler of the invention and being taken out of the rabbit killed after the lapse of one month.

FIG. 4 is a microphotograph (about 400 magnifications) of a decalcified histological specimen obtained by cutting the femur of a rabbit after one month from the operation. In view of the fact that no appreciable giant cells nor membrane caused by foreign bodies was present in the vicinity of the alumina particles, it is considered that the particles have good compatibility with the living body. Although the alumina particles 1 are scattered in the granulation tissue 3, no new bone is formed in the neighbourhood thereof. Nevertheless a few new cancellous bones 2 which are considered to be formed under the stimulation of the injected paste is observed at the vicinity of the cortical bone 7, it is seen that the alumina particles 8 have no osteogenic capacity (Under a certain stimulation, some new bones are formed in the bone-marrow.)

COMPARATIVE EXAMPLE 2

Figure 5:
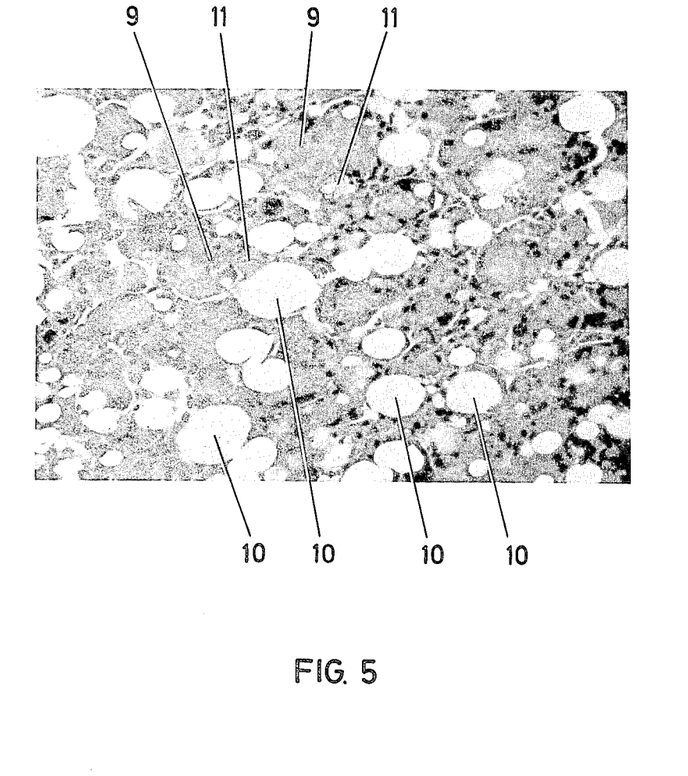
FIG. 5 is a microphotograph similar to FIG. 4, but showing the femur having a hole with a commercially available organic bone cement in place of the alumina powder.

A paste was prepared from a commercially available organic bone cement powder (produced by Howmedica Co.; a polymethylmethacrylate resin sold under the Trade Name of "Simplex"). This paste was injected into the bone-marrow of the femur of a rabbit similarly as in the preceding Examples, and the histological change of the injected portion was observed. FIG. 5 shows a microphotograph (about 200 magnifications) of a decalcified histological specimen of the injected portion after one month from the operation.

The bone-marrow of the femur injected with the bone cement paste is filled with giant cells 9 caused by foreign bodies shows the intensive foreign body reaction, and no formation of new bone is observed anywhere. It is also observed that the particles 11 of the Simplex are present scatteringly and fat spots 10 are present here and there.

EXAMPLE 6

An apatite calcium phosphate compound having the molar ratio of m/n=1.67 and prepared by the wet process was baked at 500° C. for one hour and was pulverized to obtain powders. The powders were then granulated by means of a granulator to give granules each having a diameter of from 0.3 to 1.0 mm. The granules were further baked at 500° C., 700° C., 1000° C., 1250° C. and 1350° C. for three hours, respectively, to give baked beads.

Each of the baked beads was filled in a defect (3 mm $\phi$) artificially made in cortical bone of the femur of a rabbit. Similarly to Example 3, the filled portions were observed after two weeks. In the cases where the beads baked at temperatures of from 700° C. to 1250° C. were used, it was observed that a lot of new bones were formed with osteoblasts adhering to the surfaces of the beads and the pores inside the beads. There were observed no giant cells caused by foreign body reaction. In the cases where the beads baked at 500° C. and 1350° C. were used, it was found that the amount of new bones formed was far smaller than those in the cases where the beads baked at 700° C. to 1250° C. were used although there were observed no giant cells caused by foreign body reactions.

EXAMPLE 7

An apatite calcium phosphate compound having the molar ratio of m/n=1.67 and prepared by the wet process was dried, pulverized and baked for three hours at 300° C., 500° C. 700° C., 1000° C., 1250° C. and 1350° C., respectively. The baked powders were then granulated by means of a granulator while atomizing water to give granules each having a diameter of 0.3 to 1.0 mm.

Each of the granules was then filled in a defect (2 mm$\phi$) artificially made in cortical bone of the rabbit femur. Similarly to Example 3, the filled portions were observed after two weeks.

The observation showed that the granules filled in did not retain their original granular forms but they were as if powders had been filled in. It was found that where the granules baked at 700° C. to 1250° C. were applied, there were a lot of osteoblasts and new bones formed in the vicinity of the granules and that giant cells were not found at all.

In the case where the granules baked at 300° C. were applied, the formation of new bones was observed only a little and there were observed many giant cells caused by foreign body reactions.

In the cases where the granules baked at 500° C. and 1350° C. were used, respectively, it was observed that the formation of new bones was far smaller than those in the cases where the sample powders baked at 700° C. to 1250° C. were used although giant cells caused by foreign body reactions were not observed.

EXAMPLE 8

Hydroxyapatite was prepared by the dry method by baking the same at 1200° C. for one hour and screened through a net of 149 μm meshes. To 10 g of the hydroxyapatite sample powders thus prepared were added 2 g of beads baked at 1000° C. in accordance with Example 6 to obtain a mixture of beads and powders, which was fluidized by the addition of an isotonic sodium chloride solution. The fluidized mixture was filled in a defect (3 mm $\phi$) artificially made in cortical bone of the rabbit femur.

Similarly to Example 6, the formation of new bones was observed to reveal that there were a lot of new bones formed on the surfaces and in the pores of the baked beads and in vicinity of the powders.

Although the present invention has been described with reference to the specific examples thereof, it should be understood that various modifications and variations can be easily made by those skilled in the art without departing from the spirit of the invention. Accordingly, the foregoing disclosure should be interpreted as illustrative only and not to be interpreted in a limiting sense. The present invention is limited only by the scope of the following claims.

What is claimed is:

1. A filler for filling in defects or hollow portions of bones to coalesce with the bone tissues wherein said filler is fluidized or plasticized by the addition of one selected from the group consisting of water and an isotonic sodium chloride solution, consisting essentially of powders of a calcium phosphate compound having the apatite crystalline structure of each crystallite size of 400 Å or larger and of each crystal grain size of 3 microns or smaller, said calcium phosphate compound being represented by the following general formula of $Ca_m(PO_4)_nOH$ (1.33 $\leq$ m/n $\leq$ 1.95);

said calcium phosphate compound being prepared by baking at a temperature of from 700° C. to 1250° C., and said calcium phosphate compound having a calcium ion concentration of from 3 to 5 ppm and a phosphoric ion concentration of from 1 to 4 ppm when dissolved into an isotonic sodium chloride solution and measured after 1 to 72 hours.

2. A filler for filling in defects or hollow portions of bones to coalesce with the bone tissues wherein said filler is fluidized or plasticized by the addition of one selected from the group consisting of water and an isotonic sodium chloride solution followed by granulation, consisting essentially of powders of a calcium phosphate compound having the apatite crystalline structure of each crystallite size of 400 Å or larger and of each crystal grain size of 3 microns or smaller, said calcium phosphate compound being represented by the following general formula of:

$Ca_m(PO_4)_nOH$ (1.33 $\leq$ m/n $\leq$ 1.95);

said calcium phosphate compound being prepared by baking at a temperature of from 700° C. to 1250° C., and said calcium phosphate compound having a calcium ion concentration of from 3 to 5 ppm and a phosphoric ion concentration of from 1 to 4 ppm when dissolved into an isotonic sodium chloride solution and measured after 1 to 72 hours.

3. A filler for filling in defects or hollow portions of bones to coalesce with the bone tissues wherein said filler is fluidized or plasticized by the addition of one selected from the group consisting of water and an isotonic sodium chloride solution followed by granulation and subsequent baking, consisting essentially of powders of a calcium phosphate compound having the apatite crystalline structure of each crystallite size of 400 Å or larger and of each crystal grain size of 3 microns or smaller, said calcium phosphate compound being represented by the following general formula of:

$$Ca_m(PO_4)_nOH \ (1.33 \leq m/n \leq 1.95)$$

said calcium phosphate compound being prepared by baking at a temperature of from 700° C. to 1250° C., and said calcium phosphate compound having a calcium ion concentration of from 3 to 5 ppm and a phosphoric ion concentration of from 1 to 4 ppm when dissolved into an isotonic sodium chloride solution and measured after 1 to 72 hours.

4. A filler comprising the mixture of the filler according to claim 1 and the bead-form filler according to claim 3.

5. A filler as claimed in claim 4, wherein 30% by weight or less of the baked beads are mixed based on the total weight.

6. A filler for filling in defects or hollow portions of bones to coalesce with the bone tissues wherein said filler is granulated and baked to form beads, consisting essentially of powders of a calcium phosphate compound having the apatite crystalline structure of each crystallite size of 400 Å or larger and of each crystal grain size of 3 microns or smaller, said calcium phosphate compound being represented by the following general formula of:

$$Ca_m(PO_4)_nOH \ (1.33 \leq m/n \leq 1.95);$$

said calcium phosphate compound being prepared by baking at a temperature of from 700° C. to 1250° C., and said calcium phosphate compound having a calcium ion concentration of from 3 to 5 ppm and a phosphoric ion concentration of from 1 to 4 ppm when dissolved into an isotonic sodium chloride solution and measured after 1 to 72 hours.

7. The filler as claimed in claim 1, wherein the particle size distribution of said powders of said calcium phosphate compound is such that powders each having the particle size of 300 microns or less occupy 70% or more of the total weight.

8. The filler as claimed in claim 6, wherein 70% by weight or more of said powders each have the particle size of 150 microns or less.

9. The filler as claimed in claim 1, wherein said calcium phosphate compound is an artificially synthesized compound prepared by the wet, dry or hydrothermal process.

10. The filler as claimed in claim 1, wherein there is added cancellous bone to said fillers.

11. The filler as claimed in claim 10, wherein said cancellous bone is an autoplastic bone.

12. The filler as claimed in claim 10, wherein said cancellous bone is taken up from a foreign source and the added amount of said cancellous bone is 50% by weight or less.

* * * * *